United States Patent [19]
Bolea

[11] Patent Number: 6,063,591
[45] Date of Patent: *May 16, 2000

[54] SYSTEM FOR MEASURING THE EFFICACY OF A STERILIZATION CYCLE

[75] Inventor: Phillip A. Bolea, White Bear Lake, Minn.

[73] Assignee: 3M Innovative Properties Company, St. Paul, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/078,219

[22] Filed: May 13, 1998

Related U.S. Application Data

[63] Continuation-in-part of application No. 08/856,104, May 14, 1997.

[51] Int. Cl.⁷ .............................. C12Q 1/22; C12N 11/14; G01N 21/64; C12M 1/40

[52] U.S. Cl. .................. 435/31; 435/176; 435/288.1; 435/288.7; 422/82.08

[58] Field of Search ......................... 435/31, 176, 287.4, 435/287.9, 288.1, 288.7; 422/82.08; 436/172

[56] References Cited

U.S. PATENT DOCUMENTS

| | | | |
|---|---|---|---|
| 3,542,515 | 11/1970 | Scott | 23/230 |
| 3,701,601 | 10/1972 | Plumpe, Jr. et al. | 356/96 |
| 3,776,817 | 12/1973 | Van Der Pfordten | 195/103.5 |
| 3,928,140 | 12/1975 | Wyatt et al. | 195/103.5 |
| 3,983,006 | 9/1976 | Acker et al. | 195/103.5 |
| 3,999,948 | 12/1976 | Deindoerfer et al. | 23/230 |
| 4,043,756 | 8/1977 | Sommervold | 23/230 |
| 4,055,752 | 10/1977 | Kappe et al. | 364/551 |
| 4,056,361 | 11/1977 | Peters et al. | 23/259 |
| 4,528,268 | 7/1985 | Andersen et al. | 435/31 |
| 4,579,823 | 4/1986 | Ryder | 435/296 |
| 4,626,684 | 12/1986 | Landa | 250/328 |
| 5,030,832 | 7/1991 | Williams et al. | 250/458.1 |
| 5,035,861 | 7/1991 | Grandone | 422/64 |
| 5,063,297 | 11/1991 | Hardenbroock et al. | 250/458.1 |
| 5,073,488 | 12/1991 | Matner et al. | 435/31 |
| 5,156,976 | 10/1992 | Slovacek et al. | 436/164 |
| 5,164,301 | 11/1992 | Thompson et al. | 435/29 |
| 5,167,923 | 12/1992 | Van Iperen | 422/58 |
| 5,173,434 | 12/1992 | Morris et al. | 436/172 |
| 5,223,401 | 6/1993 | Foltz et al. | 435/18 |
| 5,244,637 | 9/1993 | Pratellesi et al. | 422/102 |
| 5,252,484 | 10/1993 | Matner et al. | 435/288 |
| 5,324,635 | 6/1994 | Kawase et al. | 436/7.94 |
| 5,334,841 | 8/1994 | Graessle et al. | 250/458.1 |
| 5,340,747 | 8/1994 | Eden | 436/172 |
| 5,374,395 | 12/1994 | Robinson et al. | 422/64 |
| 5,418,167 | 5/1995 | Matner et al. | 435/288 |
| 5,432,061 | 7/1995 | Berndt et al. | 435/34 |
| 5,456,883 | 10/1995 | Burkovich et al. | 422/64 |
| 5,474,910 | 12/1995 | Alfano | 435/34 |
| 5,480,804 | 1/1996 | Niwa et al. | 435/286.1 |
| 5,486,459 | 1/1996 | Burnham et al. | 435/31 |
| 5,525,466 | 6/1996 | Slovacek et al. | 435/6 |
| 5,565,634 | 10/1996 | Graessle et al. | 73/865.9 |
| 5,573,950 | 11/1996 | Graessle et al. | 435/287.3 |
| 5,580,784 | 12/1996 | Berndt | 435/288.7 |
| 5,593,854 | 1/1997 | Berndt | 435/31 |
| 5,779,983 | 7/1998 | Dufresne et al. | 422/102 |
| 5,830,683 | 11/1998 | Hendricks et al. | 435/31 |
| 5,863,790 | 1/1999 | Bolea | 435/287 |

FOREIGN PATENT DOCUMENTS

| | | | |
|---|---|---|---|
| 0 607 941 A2 | 7/1994 | European Pat. Off. | G01N 21/64 |
| WO 95/08639 | 3/1995 | WIPO | C12Q 1/22 |

OTHER PUBLICATIONS

Lehninger, A.L. Biochemistry, second ed. Worth Publishers, New York. (1975), pp. 186–195. No month found.

Merriam–Webster's Dictionary, tenth edition, p. 285. Merriam–Webster, Inc. Springfield, MA. (1996). No month found.

Vesley et al. "Fluorimetric Detection of a *Bacillus stearothermophilus* Spore–Bound Enzyme, α–D–Glucosidase, for Rapid Indication of Flash Sterilization Failure", Applied and Environmental Microbiology, vol. 58, No. 2, Feb. 1992, pp. 717–719.

Guilbault et al. "Fluorometric Procedure for Measuring the Activity of Dehydrogenases", Analytical Chemistry, vol. 37, No. 10, Sep. 1965, pp. 1219–1221.

Guilbault et al. "New Direct Fluorometric Method for Measuring Dehydrogenase Activity", Analytical Chemistry, vol. 36, No. 13, Dec. 1964, pp. 2497–2498.

"3M Attest Rapid Readout Biological Monitoring System for 250° F./121° C. C Gravity, 270° F./132° C. Vacuum Assisted Sterilizers", 3M Health Care, 1995.

"Attest Rapid Readout Biological Monitoring System for 270° F.132° C. Gravity Displacement Steam (flash) Sterilizers", 3M Health Care, 1993.

"Attest Rapid Readout Biological Monitoring System for 270° F./132° C. Gravity Displacement Steam Sterilization", 3M Health Care, Sep. 1990.

"Attest Biological Monitoring System", 3M Health Care (brochure—admitted prior art).

*Primary Examiner*—Ralph Gitomer
*Assistant Examiner*—Marjorie A. Moran
*Attorney, Agent, or Firm*—Jeffrey J. Hohenshell

[57] ABSTRACT

A system is used for determining efficacy of a sterilization cycle. A biological sterilization indicator exhibits fluorescence in response to biological activity which is indicative of bacterial growth in the biological sterilization indicator. The biological sterilization indicator is exposed to the sterilization cycle and is placed in a fluorescence reading apparatus. The fluorescence from the biological sterilization indicator is read to obtain a first fluorescence reading. The fluorescence from the biological sterilization indicator is re-read to obtain a second fluorescence reading. The efficacy of the sterilization cycle is determined based on the first and second fluorescence readings.

22 Claims, 9 Drawing Sheets

SYSTEM FOR MEASURING THE EFFICACY OF A STERILIZATION CYCLE

CROSS REFERENCE TO RELATED APPLICATIONS

This application is a continuation-in-part of U.S. patent application Ser. No. 08/856,104, filed May 14, 1997.

BACKGROUND

The present invention relates to a system for determining the efficacy of a sterilization cycle. More specifically, the present invention relates to a system for reading fluorescence from a biological sterilization indicator in order to determine the efficacy of the sterilization cycle.

The sterilization of equipment and devices is critical in some industries. For example, hospitals and other medical institutions must commonly and frequently sterilize equipment and devices used in treating patients. The particular type of sterilization cycle used to sterilize such equipment can vary based on the particular equipment or devices being sterilized and based on the particular preference of the entity performing the sterilization cycle. However, all such sterilization cycles or processes are typically designed to kill living organisms which might otherwise contaminate the equipment or devices being sterilized.

Various sterilization cycles use different methods or techniques for sterilization. For instance, such sterilization cycles may include the administration of steam, dry heat, chemicals, or radiation, to the equipment or devices being sterilized. Steam sterilization is typically efficacious when the equipment being sterilized are exposed to steam having a temperature in a range of 121–132° C. The equipment being sterilized are preferably exposed to the steam sterilization for approximately three minutes at 132° C., and ranging to 30 minutes at 121° C. One form of chemical sterilization involves exposing the devices to be sterilized to ethylene oxide gas. The devices being sterilized are exposed to the ethylene oxide gas for approximately one hour at 65° C. to approximately four hours at 30° C. Dry heat sterilization typically involves exposing the devices being sterilized to temperatures in a range of approximately 180° C., or higher, for at least two hours. In many environments, the efficacy of the sterilization cycle is critical. Therefore, sterilization indicators are used to determine the efficacy of the sterilization cycle.

Sterilization indicators have taken a number of forms in the past. For example, biological indicators and chemical indicators are well known in the art. In conventional biological indicators, a test organism which is many times more resistant to the sterilization process than most organisms which would be present by natural contamination, is coated on a carrier and placed in a sterilizer along with the articles to be sterilized. Thus, the sterilization indicator is exposed to the same sterilization cycle as the devices being sterilized. After completion of the sterilization cycle, the carrier is incubated in nutrient medium to determine whether any of the test organisms survived the sterilization procedure. In the conventional biological sterilization indicators, growth of a detectable number of organisms normally takes at least approximately 24 hours.

The biological sterilization indicator is then examined to determine whether such growth has taken place. If so, such growth indicates that the sterilization cycle has not been efficacious, and it can be assumed that the devices which were subject to the sterilization cycle are not sterile.

Commercially available chemical indicators utilize chemicals which indicate sterility by color changes, or change from a solid to liquid state. One advantage to such chemical indicators is that the results are known by the end of the sterilization cycle. However, the results only indicate, for example, that a particular temperature has been reached for a certain period of time, or that ethylene oxide gas was present, during the sterilization cycle. Arguably, chemical indicators do not necessarily indicate whether conditions necessary for eliminating the organisms of interest have been achieved. Thus, the industry has shown a preference for biological indicators that use living organisms.

Sterilization indicator technology is disclosed in Matner et al. (U.S. Pat. Nos. 5,073,488; 5,252,484 and 5,418,167) and Foltz et al. U.S. Pat. No. 5,223,401 (the entire contents of each of which are herein expressly incorporated by reference). Those patents describe sterilization indicators having enzymes which drastically reduce the time required to indicate the effectiveness of the sterilization cycle.

Commercial examples of biological indicators with rapid response times include the 3M™ Attest™ Rapid Readout Biological Indicators available from 3M of St. Paul, Minn. (USA). The Attest Rapid Readout Biological Indicators include a flexible polypropylene vial with a spore strip which has a viable population of *Bacillus Stearothermophilus* spores. The vial also contains a growth medium which is a modified tryptic soy broth contained in a crushable glass ampule. With the Attest Rapid Readout Indicator designed for use with a steam sterilization cycle, the presence of a spore-associated enzyme indicates spore growth in the biological indicator. The presence of the active enzyme is measured by using a nonfluorescent substrate. The nonfluorescent substrate is converted by the active spore-associated enzyme to a fluorescent product.

If the sterilization cycle is not efficacious, both the spore and the enzyme remain active. The enzyme converts the substrate to a fluorescent product. Therefore, the fluorescence in the vial is detected, after an incubation period, to determine the efficacy of the sterilization cycle.

While 3M™ Attest™ Rapid Readout Biological Indicators significantly advanced the art, there is room for improvement. In order to detect spore growth activity through fluorescence, the Rapid Readout Biological Indicators for steam sterilization cycles typically incubate for one hour. After the incubation time, the vial is placed in a reading apparatus and the fluorescence within the vial is read. The incubation time required to obtain an accurate reading in such a prior reading apparatus could be shortened.

The prior reading apparatus associated with 3M™ Attest™ Rapid Readout Biological Indicators should be calibrated after a predetermined time out period (such as 12 hours of operation) or whenever power is interrupted to the unit. The calibration process has multiple operator steps. Further, the calibration is performed using a biological indicator which has been subjected to the sterilization cycle, and which is assumed to be sterile. Arguably, the calibration is essentially performed against an unknown value.

SUMMARY OF THE INVENTION

The present invention arises, in part, from the realization that the method of reading the biological indicator in the prior art readers was not as efficient as it might be. The various components of the biological indicator (such as the vial, the spore strip, the cap, and the packaging) all exhibit autofluorescent behavior which has nothing to do with the spore growth activity contained in the biological indicator vial. Therefore, this autofluorescent behavior acts as a baseline or threshold fluorescence reading during fluorescence detection.

In prior systems, each biological indicator was assumed to have the worst case autofluorescent behavior associated with that particular type of biological indicator. The fluorescence from the biological indicator was read and it was determined whether that fluorescence exceeded the baseline, worst case autofluorescence. Therefore, the spore growth activity had to reach such a level that the fluorescence created by the spore growth exceeded the worst case autofluorescent behavior which could be exhibited by the biological indicator vial. This lengthened the time associated with a determination of the efficacy of the sterilization cycle.

With the present invention, a baseline fluorescence reading is taken for each biological indicator prior to incubation. That fluorescence reading is used as a baseline or threshold fluorescence reading for that particular biological indicator. Therefore, after a short incubation time, another fluorescence reading is taken, and it is determined whether the fluorescence in the biological indicator has changed by a statistically significant amount over that evidenced by the first fluorescence reading. The efficacy of the sterilization cycle is determined based on the readings. The time to a non-efficacious reading is a function of the number of viable organisms in the biological indicator. This can be as short as ten minutes. Time to an efficacious indication is a function of the type of assay and is preferably established empirically.

In a preferred embodiment, as soon as it is determined that the fluorescence in the biological indicator has changed by a statistically significant amount over the baseline reading taken from the biological indicator, it is determined that the sterilization cycle was not efficacious.

DETAILED DESCRIPTION

Figure 1A:
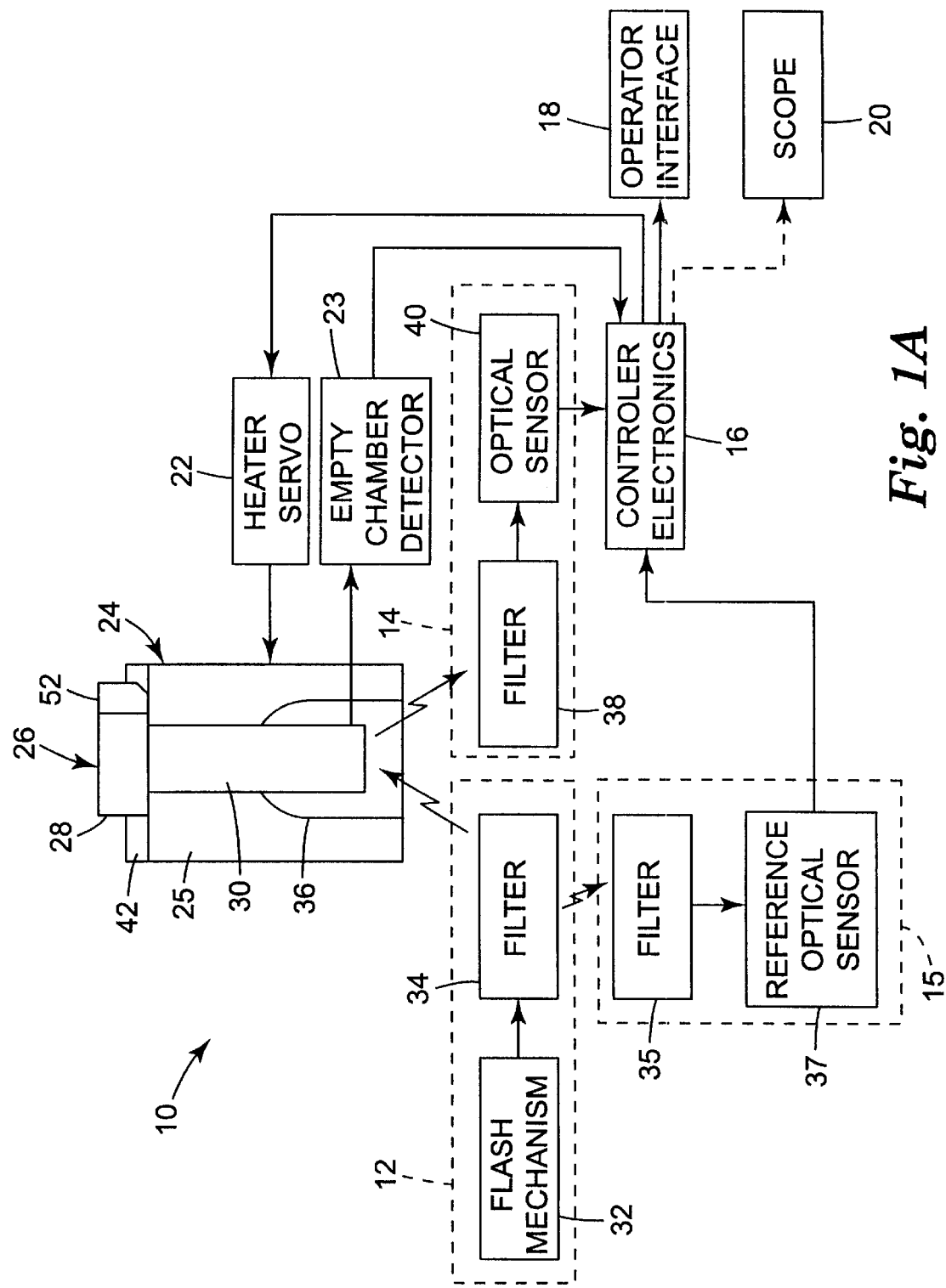
FIG. 1A is a block diagram of a biological indicator reading system in accordance with the present invention.

FIG. 1A is a block diagram of a biological indicator reading system 10 (system 10) in accordance with one aspect of the present invention. System 10 includes electro-optical excitation module 12, electro-optical sensing module 14, reference module 15, controller electronics 16, operator interface 18, optional scope 20, heater servo 22, empty chamber detector 23 and incubator and optical integration cavity 24 (incubator 24) which includes incubator module 25 and optical integration cavity 36 formed therein. System 10 also illustrates a biological sterilization indicator 26 (BI 26) with antirotational feature on its cap 28 seated within incubator 24.

In the preferred embodiment, BI 26 is a biological sterilization indicator commercially available from the Minnesota Mining and Manufacturing Company of St. Paul, Minn., under the trade name, 3M Attest, models 1291 or 1292. BI 26 includes cap 28, vial 30 and various contents (not shown). BI 26 evidences the presence of a viable microorganism (such as spores) by the production of fluorescence within vial 30 after incubation in incubator 24. This is preferably accomplished by utilizing a non-fluorescent substrate (such as 4-methylumbelliferyl-alpha-D-glucoside) in vial 30 and converting that non-fluorescent substrate to a fluorescent product by spore-associated enzyme activity. The spore-associated enzyme is preferably alpha-D-glucosidase, which is one of the enzymes involved in the growth of the spore within vial 30.

In order to take a fluorescence reading from BI 26, electro-optical excitation module 12 provides optical excitation to the fluorescent substances in vial 30 and to reference module 15. Electro-optical excitation module 12 preferably includes a flash mechanism 32 and a filter 34. Flash mechanism 32, in one preferred embodiment, is a flash tube which emits a broadband light pulse (as approximately a 100 $\mu$s pulse) which is rich in the near ultra-violet range of wavelengths. Alternatively, a cold cathode flourescent lamp may be used instead of the flash tube. This is a continuous wave type device. A commercially available example of such a device is the JKL BF350-UV351 available from JKL Corp. of California, U.S.A.

Filter 34 is preferably an absorptive color glass filter which exhibits low autofluorescence and passes selected wavelengths. A suitable filter is a Schott bg 39, ug 11 filter which is available from Schott Glass Technologies, Inc. of Duryea, Pa.

The light is passed through filter 34 and impinges on vial 30 and reference module 15. Reference module 15 preferably includes filter 35 and reference optical sensor 37. Filter 35 is preferably a filter, or set of filters, which is chosen to pass the excitation energy which passes through filter 34. Filter 35 passes this energy to reference optical sensor 37. A suitable filter is a Schott bg 39, ug 11 filter which is available from Schott Glass Technologies, Inc. of Duryea, Pa.

Reference optical sensor 37 senses the energy passing through filter 35 and provides a reference signal to controller electronics 16 which is indicative of the energy passing through filter 35. Thus, the reference signal provided to controller electronic 16 by reference optical sensor 37 is indicative of the intensity of the flash emitted by flash mechanism 32.

The light which is passed through filter 34 and impinges on vial 30 excites the fluorescence material in vial 30. The fluorescence emitted from vial 30 is preferably collected by an integration cavity 36 which is preferably a geometric reflective cavity (such as parabola or sphere shaped) arranged about vial 30 to collect (or integrate) the fluorescence emitted from vial 30 and to direct that fluorescence to electro-optical sensing module 14.

Electro-optical sensing module 14 includes filter 38 and optical sensor 40. Filter 38 is preferably a filter, or a set of filters, which is chosen to reject surface reflection from the surface of vial 30 when the flash impinges on the surface of vial 30. A suitable filter blocks light in approximately the 350 nm wavelength range and passes light in approximately the 450 nm wavelength range. Any suitable filtering can be used which tends to reduce interference between the excitation energy from flash mechanism 32 and the emission energy from vial 30. This filter acts to pass the emission wavelengths which are indicative of fluorescence in vial 30. One suitable filter used as filter 38 is provided by Schott Glass Technologies, Inc. as a Schott bg 39, kv 408 filter. The output of filter 38 is provided to optical sensor 40 which is preferably a blue enhanced photodiode which enhances the sensitivity of the photodiode in the 400–450 nm wavelength range. One suitable optical sensor 40 is provided by Burr Brown Corporation of Tucson, Ariz. under the trade name OPT 301.

The output of optical sensor 40 is provided to controller electronics 16. In the preferred embodiment, controller electronics 16 is a microprocessor based controller which includes associated memory and timing circuitry and amplifiers and other suitable conditioning circuitry for receiving the outputs from optical sensors 37 and 40 and providing them as conditioned signals indicative of the intensity of flash mechanism 32 and of the fluorescent activity in vial 30, respectively. Controller electronics 16 also preferably includes connection to a suitable operator interface 18. In the preferred embodiment, operator interface 18 includes a CRT and keyboard, or a membrane keypad input, a touch screen input or any other suitable operator interface device. Controller electronics 16 may be connected to optional scope 20 which is a commercially available oscilloscope used to provide a display indicative of the signal received from the optical sensor 40. Finally, controller electronics 16 is also preferably coupled to heater servo 22 and empty chamber indicator 23.

Heater servo 22 is preferably a programmable, or otherwise suitable, heater device which provides heat to incubator 24 which is used to incubate the spores and growth medium in BI 26. The amount of heat provided by heater servo 22 will depend on the specific biological make up of the substances in BI 26, as is known in the art. Also, multiple heater zones having operational set points which are determined based on specific user defined BI models can also be used.

Empty chamber detector 23 detects whether a BI 26 is in incubator 24. Detector 23 is discussed in greater detail with respect to FIG. 1C below.

The items which comprise BI 26 exhibit autofluorescent behavior when excited by electro-optical excitation module 12. For example, it has been found that some biological indicators exhibit autofluorescent behavior which provides a fluorescence reading which may be approximately five times greater than a reading from an empty reading cavity. Further, when the growth medium in vial 30 has been applied to the spore strip (i.e., when BI 26 is wet out), the autofluorescent behavior of BI 26 increases by an additional 20%. This autofluorescent behavior acts as a baseline or threshold reading for each biological indicator. Therefore, in prior systems, the reading apparatus would require the spore growth activity in the biological indicator to cause fluorescence which exceeded a worst case threshold expected for any biological indicator useable with that reading apparatus.

In accordance with one aspect of the present invention, shortly after the growth medium is applied to the spore strip in BI 26, but prior to any significant incubation, a fluorescence reading is taken and is correlated to that specific BI 26. Then (as described in greater detail later in the specification) after some incubation time another fluorescence reading is taken from that particular BI 26 and it is compared to the first or baseline reading for that particular BI 26. Controller electronics 16 then determines whether the second fluorescence reading has exceeded the first fluorescence reading by a statistically significant amount. If so, controller electronics 16 provides an output to operator interface 18 indicating that there is spore growth activity in BI 26, and thus the sterilization cycle through which BI 26 has gone was not efficacious.

In performing this procedure, there are a number of different ways that the fluorescence reading can be taken from BI 26. FIG. 1A illustrates a preferred embodiment in which incubator 24 has an optical collection or integration cavity 36. This type of cavity includes a reflector arranged about vial 30 which acts to collect or integrate light from around the entire outer periphery of vial 30 and direct that light toward electro-optical sensing module 14. However, another way to take a fluorescence reading from vial 30 is to focus optical sensor 40 on only a smaller portion of vial 30. In that case, fluorescent activity is sensed only from a portion of vial 30, and not from the entire external periphery of vial 30. Where this type of fluorescence reading technique is used, it is important that BI 26 (if it is removed from incubator 24 at any time during the process) be replaced in the same angular orientation relative to electro-optic sensing module 14 for the second fluorescence reading as it was for the baseline fluorescence reading. Thus, in accordance with one aspect of the present invention, BI 26 has a keying feature which requires it to assume the same angular orientation relative to electro-optic sensor module 14 each time. This is illustrated in FIG. 1B.

Figure 1B:
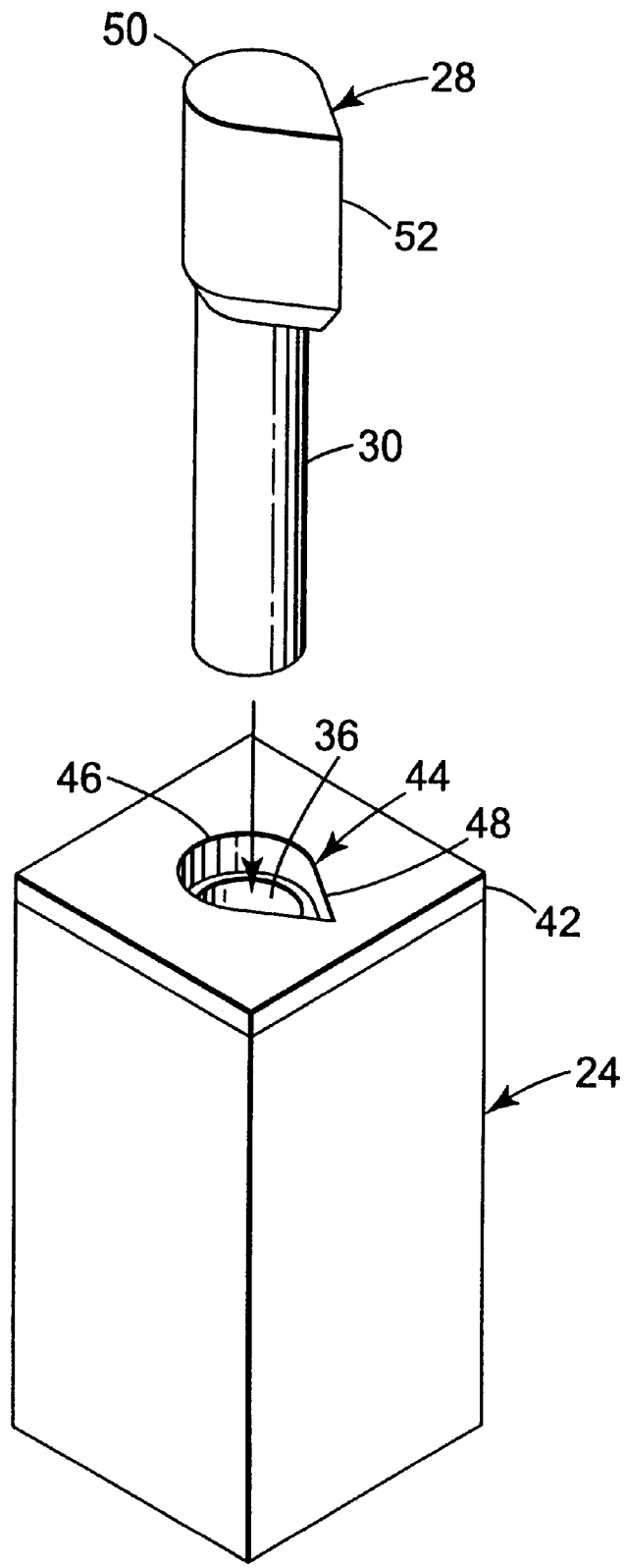
FIG. 1B is an exploded view of a portion of a biological indicator reading system in accordance with one aspect of the present invention.

FIG. 1B illustrates an exploded view of incubator 24. FIG. 1B illustrates that a key block 42 extends from an upper surface of incubator 24. Key block 42 has a cap receiving aperture 44 defined therein. Aperture 44 has a generally circular portion 46 and a key way 48. Aperture 44 is sized just larger than an outer periphery of cap 28 of BI 26. Cap 28 has an exterior periphery which is also formed of a generally circular portion 50 and a key portion or protrusion 52. By providing this arrangement, the only way that cap 28 can be inserted within block 42 is by angularly aligning key 52 with key way 48. Also, in a preferred embodiment, the bottom portion of cap 28 or key 52 is chamfered so that it seeks into key way 48. This helps to assure that vial 30 is inserted and held within incubator 24 in the same angular orientation each time. This increases the consistency of fluorescence readings taken from BI 26, particularly when no integration cavity 36 is used.

Figure 1C:
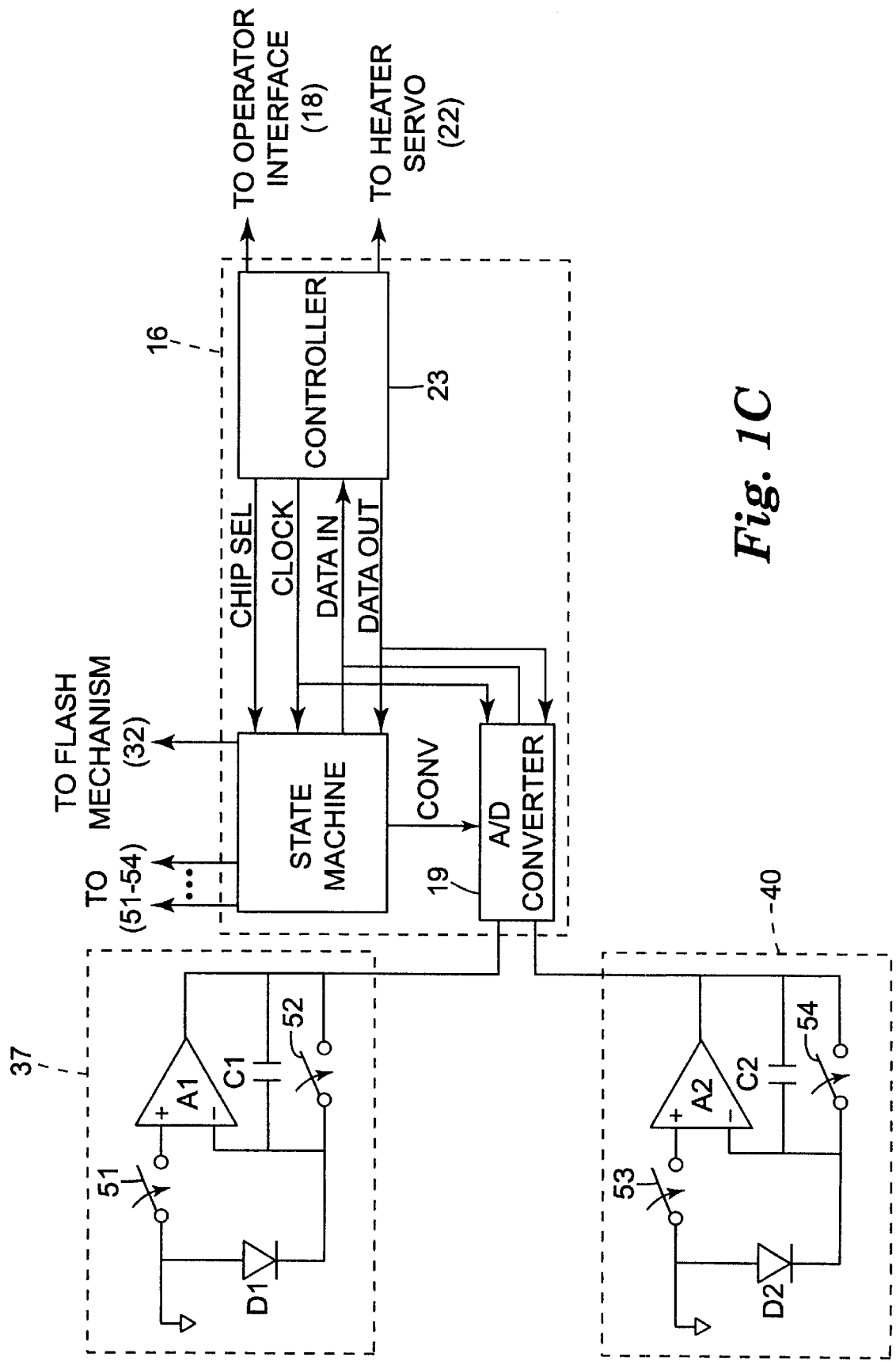
FIG. 1C is a more detailed block diagram of a portion of the reading system shown in FIG. 1A, in partial schematic form.

FIG. 1C is a more detailed block diagram of a portion of system 10 shown in FIG. 1A. FIG. 1C illustrates a portion of reference optical sensor 37, optical sensor 40, and controller electronics 16 in greater detail. Reference optical sensor 37 includes photodiode D1, switches S1 and S2, capacitor C1 and amplifier A1. Optical sensor 40 includes diode D2, switches S3 and S4, capacitor C2 and amplifier A2. Controller electronics 16 includes analog-to-digital (A/D) converter 19, state machine 21 and controller 23.

Photodiode D1 in reference optical sensor 37 is arranged to sense the excitation energy emitted by filter 34 from flash mechanism 32. Therefore, photodiode D1 is preferably either arranged to receive light directly from filter 34, or excitation light which is reflected off of the vial 30 and integration cavity 36. In any case, photodiode D1 is placed adjacent suitable filter 35 such that only energy in a range near the wavelength of excitation energy provided by flash mechanism 32 is passed.

Photodiode D2, on the other hand, is arranged relative to integration cavity 36 and vial 30 to detect emission energy which is emitted from cavity 36 and vial 30 based on the fluorescent behavior of BI 26. Therefore, an appropriate filter 38 is provided to pass only the wavelengths in a range corresponding to the fluorescence from vial 30.

By providing both a reference optical sensor 37 and optical sensor 40, a number of things are accomplished. First, the light pulse provided by flash mechanism 32 is not completely constant from flash-to-flash. In other words, the light output by flash mechanism 32 is somewhat dependent on the temperature of the plasma arc in the lamp. Therefore, flashes can exhibit some variation in spectral content, from flash-to-flash. If a first flash is directed at vial 30, the fluorescent activity may be one level, while if a second flash (more intense than the first flash) is directed at the same vial 30, the fluorescent behavior of the substance in vial 30 may be different. By providing reference optical sensor 37, the signal representing the fluorescent energy emitted by vial 30 can be normalized using the specific reference signal from reference optical sensor 37 which is indicative of the intensity of that particular flash from flash mechanism 32. Thus, the varying effects of different flash intensities are substantially eliminated from further processing steps.

Also, the intensities of the flashes from flash mechanism 32 can tend to degrade over time, and eventually flash mechanism 32 becomes inoperative. By providing reference optical sensor 37 which is configured to sense the intensity of the flash from flash mechanism 32, system 10 can be configured to alert the operator when flash mechanism 32 is no longer operating sufficiently.

Further, reference optical sensor 37 is also advantageous when used in conjunction with empty chamber detector 23. Empty chamber detector 23 is configured to detect whether a BI 26 is in place within integration cavity 36. Empty chamber detector 23 can take any number of suitable forms, such as an optical detector which includes a light emitter on one side of the chamber which receives BI 26 and an optical detector on the other side. When a BI is in place within the chamber, the optical signal provided by the optical detector provide a suitable indication. Empty chamber detector 23 can also be embodied as a simple mechanical switch, or a mechanical relay type indicator which changes state based on whether a BI 26 is in the chamber. In this way, controller electronics 16 is capable of determining whether integration cavity 36 is dirty, or needs cleaning or other service. For example, when BI 26 is not located in integration cavity 36, controller electronics 16 expects to see some type of autofluorescent behavior in response to a flash from flash mechanism 32. Also, if reference optical sensor 37 is arranged to receive excitation energy reflected from integration cavity 36 (rather than directly from filter 34) controller electronics 16 can compare the expected results of a flash with the actual results of a flash to determine whether a foreign object is located in integration cavity 36, whether the walls of integration cavity 36 are coated with debris or otherwise need cleaning, or whether integration cavity 36 needs some other type of service.

In operation, the circuit set out in FIG. 1C is first initialized. Upon receiving a start signal from controller 23, state machine 21 provides signals to switches S1–S4 to open switches S1 and S3 and to close switches S2 and S4. This forces the charge in capacitors C1 and C2 to a zero level in both sensor 37 and sensor 40. Then, switches S2 and S4 are opened and switches S1 and S3 are closed. In this state, sensors 37 and 40 are monitoring for a flash.

State machine 21 then provides a flash output signal to flash mechanism 32 causing flash mechanism 32 to emit a flash. The light pulse may preferably be approximately 50–100 microseconds wide. Photodiode D1, as filtered by filter 35, responds to the excitation energy emitted by flash mechanism 32. Photodiode D2, as filtered by filter 38, responds to the emission energy emitted due to fluorescence in vial 30. In both diodes D1 and D2, photocurrent is induced in, and begins flowing in the diode by photons impinging on the photodiode. The current causes a charge to develop in capacitors C1 and C2, respectively, and causes amplifiers A1 and A2 to react positively in that the output of the amplifiers moves from approximately a zero volt level to approximately a five volt level. More specifically, the transfer function of the sensors 37 and 40 is as follows:

$$V_{out} = -1/cap \int I_{in}(t)dt$$

where $V_{out}$=the output voltage provided at the output of the amplifiers in sensors 37 and 40;

cap=the capacitance of capacitors C1 and C2, respectively, and $I_{in}(t)$=the photocurrent induced in diodes D1 and D2, respectively, by photons impinging on the photodiodes.

Next, state machine 21 provides the convert (CONV) signal to A/D converter 19. A/D converter 19 is preferably any suitable and commercially available 12 bit analog-to-digital converter which provides an output in a serial data stream. However, any other suitable A/D converter having a suitable configuration can also be used. In response to receiving the CONV signal from state machine 21, A/D converter 19 provides digital data indicative of the values of the voltages provided by sensors 37 and 40 on the DATA IN line to controller 23.

It is also worth noting that controller 23 provides data on a DATA OUT line to state machine 21 and A/D converter to configure those portions of the circuit appropriately. Also, a clock signal is provided to A/D converter 19, state machine 21 and controller 23 from a bus master (not shown) which provides synchronization and clocking in the circuit.

Figure 3:
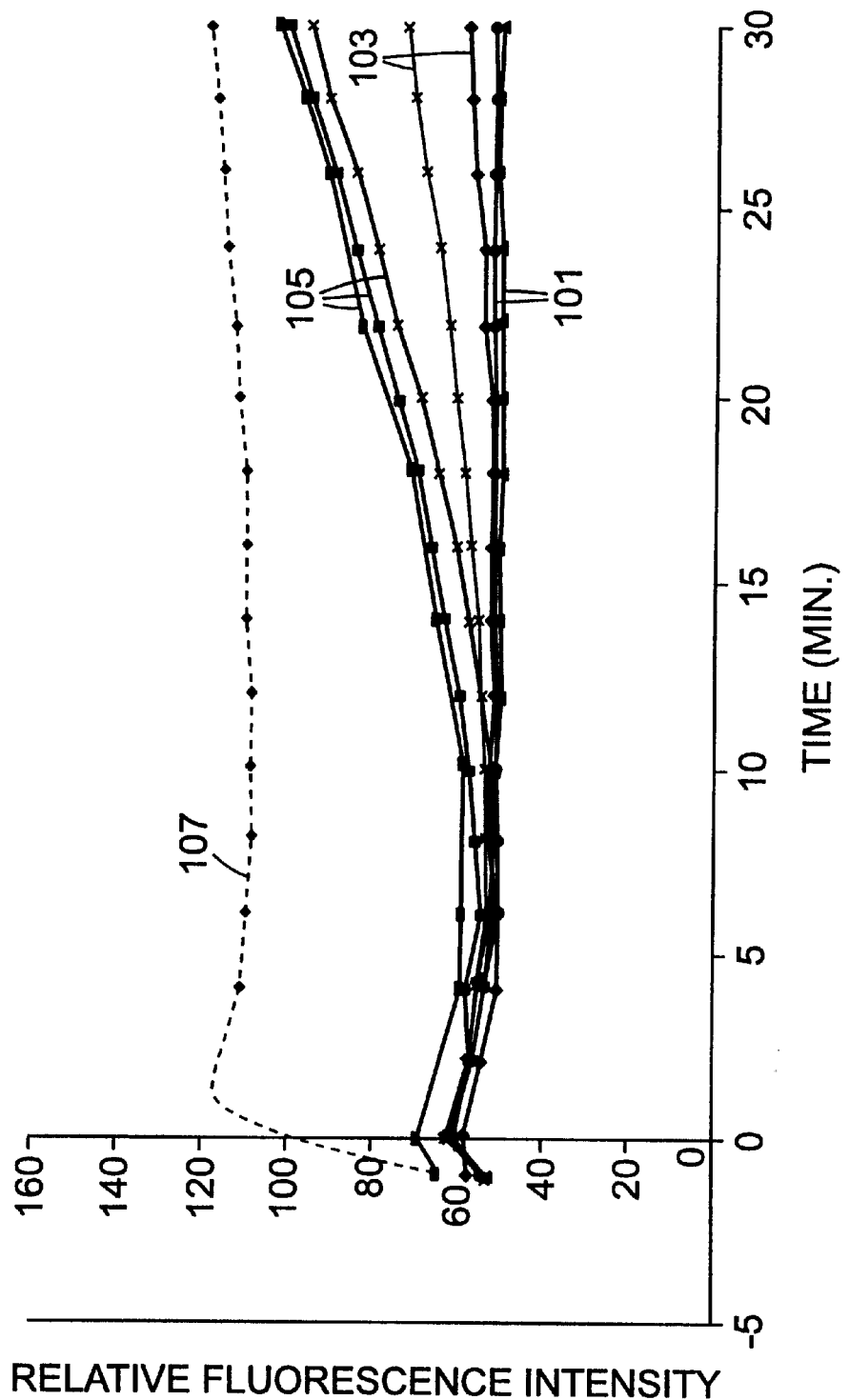
FIG. 3 illustrates a family of curves representing relative fluorescence intensity plotted against time for a plurality of different biological indicators.

After receiving the digitized signal from A/D converter 19, controller 23 provides an output signal which is indicative of the fluorescence in vial 30, taking into account the intensity of the flash emitted by flash mechanism 32 which resulted in the fluorescence. In making this calculation, controller 23, in the preferred embodiment, takes into account the kinetic series associated with a particular BI 26 being analyzed. A kinetic series, as is described in greater detail with reference to FIG. 3, is preferably an empirically generated curve, or series of curves, which graphs the relative fluorescence intensity for that particular model of BI, against time in minutes, for BIs having different levels of viable organisms after sterilization.

In providing the output signal, controller 23 first normalizes the emission data detected by optical sensor 40. This is provided by taking the reading from optical sensor 40 and subtracting the minimum value of the kinetic series associated with that particular BI. That value is then divided by the range of the kinetic series and multiplied by 100%. Thus, controller 23 is taking each reading as a percent of the full scale amplitude of the kinetic series associated with that particular BI. This eliminates incompatible units in the determination. Controller 23 then takes the resultant normalized data and corrects it for variations in the flash from flash mechanism 32. In order to do this, the corrected emission data is represented by the normalized uncorrected emission data (obtained as indicated above) divided by the normalized excitation reference data provided by optical reference sensor 37. The result is a normalized output signal connected for flash variations.

FIGS. 2A–2D illustrate the operation of system 10 in accordance with one aspect of the present invention. BI 26 is placed in a sterilizer along with the other devices or equipment to be sterilized. This is indicated by block 54. Then, the sterilization cycle is performed. The sterilization cycle may typically include steam sterilization, dry heat sterilization, or chemical (e.g. ethylene oxide, peracetic acid or hydrogen peroxide based), plasma or radiation sterilization techniques or combinations thereof. Different time frames, temperature regimes and sterilization cycles require the use of different types of BIs, as is known. In any case, BI 26 is subjected to the sterilization cycle. This is indicated by block 56.

Next, the operator inputs into system 10 (preferably through operator interface 18) the particular type of BI 26 being used in the system. This is indicated by block 57 and accomplishes a number of things. First, the particular type of BI being used indicates to controller electronics 16 the correct set point for heater servo 22 (or other heater servos in the system). For instance, one type of BI may require incubation at approximately 60° C., while another type may require incubation at approximately 37° C. In addition, based on the type or types of BI 26 being used, controller electronics 16 will retrieve from memory corresponding kinetic behavior information for use in providing the output (as discussed above and with respect to FIG. 1C). FIG. 3 illustrates such kinetic information for one particular BI. The kinetic information illustrated in FIG. 3 is for the 3M™ Attest™ Rapid Readout Biological Indicator model 1291 manufactured by Minnesota Mining and Manufacturing, of St. Paul, Minn. Time in minutes is plotted along the x-axis while relative fluorescence intensity is plotted along the y-axis. FIG. 3 illustrates a number of curves, represented by the designation numeral 101, which correspond to no viable organisms in the BI 26 after the sterilization cycle. FIG. 3 also illustrates another number of curves illustrated by reference numeral 103 which correspond to a small number of viable organisms, curves 105 which correspond to a large number of viable organisms, and curve 107 which is indicative of a contaminated BI (and which is described in greater detail below).

The fluorescence intensity readings obtained for the time just prior to time zero in FIG. 3 correspond to the autofluorescence of the biological indicator, before it is wetted out, and with the ampule still intact. At time zero, the ampule is cracked and the spore strip in the particular BI is wetted out. It will be noted that, for this model BI, over the first five or so minutes, all non-contaminated BIs are associated with curves that have a generally negative slope. In other words, for the first five minutes, the fluorescence activity in all non-contaminated BIs tends to decrease. Then, for the next several minutes, the BIs exhibit a substantially zero slope curve wherein there is no change in fluorescence activity. Thereafter, the slope of the curve depends on the number of viable organisms remaining in that particular BI after the sterilization cycle. The larger number of viable organisms remaining, the more steeply positive the slope. Therefore, once the particular BI is input by the operator, controller 23 retrieves from memory the associated kinetic characteristics, such as those set out in FIG. 3.

Figure 2A:
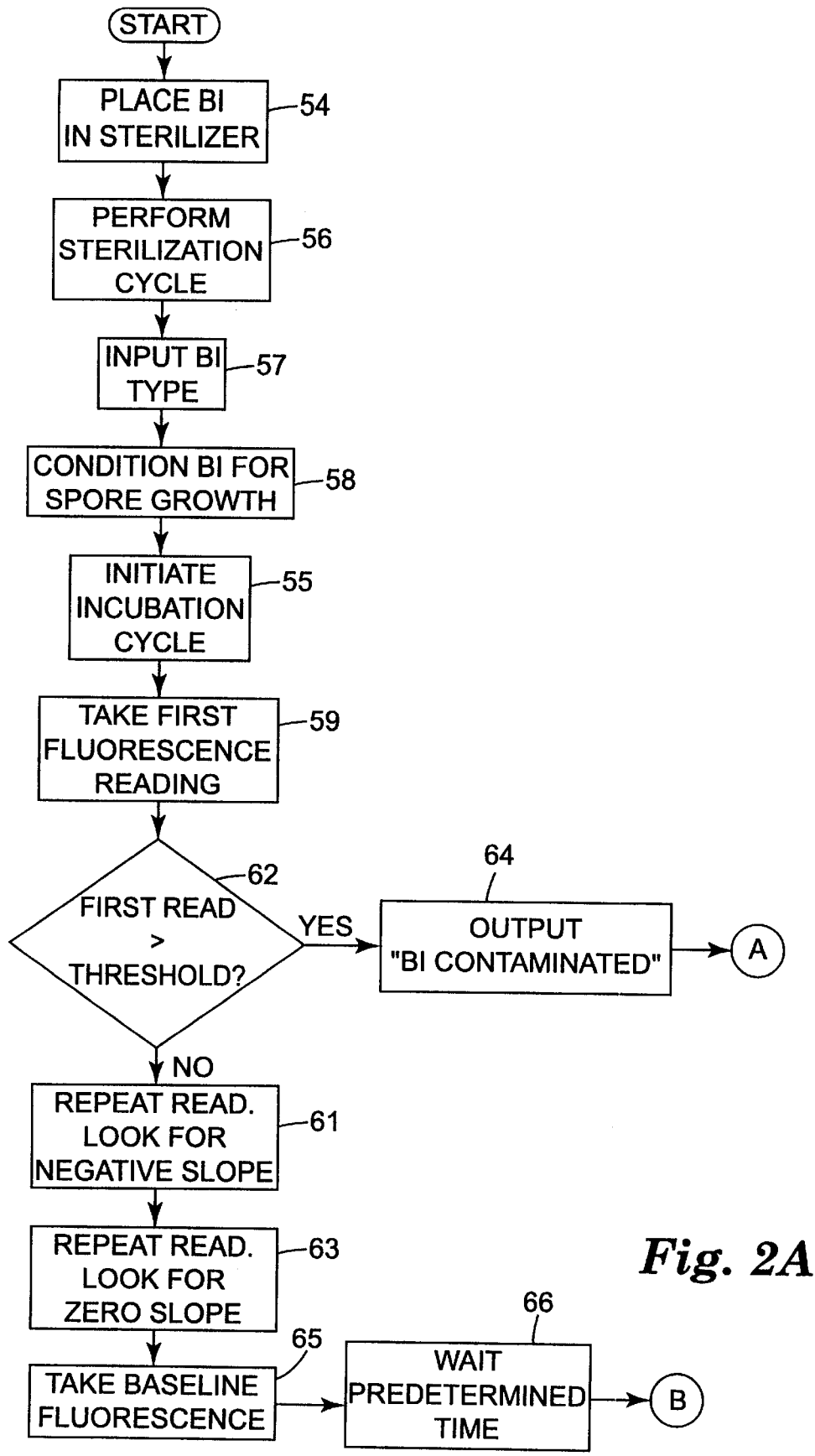
FIGS. 2A–2D illustrate the operation of a biological indicator reading system in accordance with the present invention.
Figure 2B:
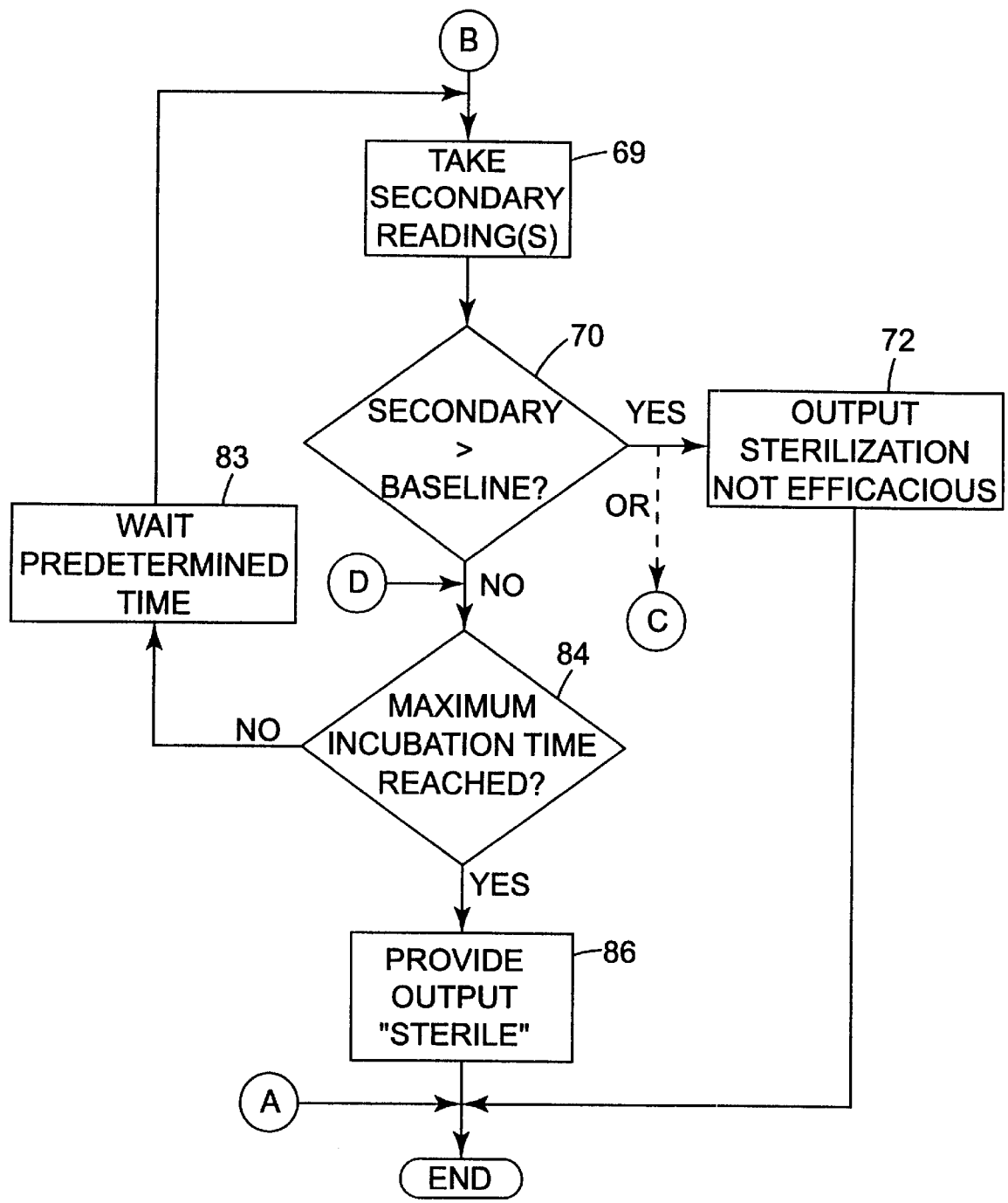

Next, BI 26 is conditioned for spore growth. In the embodiment in which BI 26 is the Attest Rapid Readout Biological Indication model 1291 BI, the glass ampule containing a growth medium is crushed and its contents are applied to a dry strip containing the spores. Referring now to FIG. 2A, conditioning of BI 26 for spore growth is indicated by block 58. BI 26 is then incubated as indicated by block 55.

A first fluorescence reading is then taken at approximately time zero in FIG. 3. This is indicated by block 59 in FIG. 2A. The fluorescence reading taken at roughly time zero is indicative of the autoflourescent behavior of the particular BI 26, at that time, for which the reading is being taken. In addition, unless BI 26 was contaminated prior to the sterilization cycle, the first reading will not include fluorescence attributable to any significant spore growth. Controller electronics 16 then compares the first fluorescence reading to a predetermined threshold level. If the first reading exceeds the threshold level, this indicates that the particular BI 26 for which the first reading is being taken has been contaminated prior to the sterilization cycle, such as at the manufacturer of that particular BI 26. In other words, if BI 26 is contaminated prior to the sterilization cycle, significant spore growth or bacterial activity will have already taken place in that BI 26 prior to any incubation. Thus, the initial first fluorescence reading will reflect quite a high degree of fluorescence, much higher than the autofluorescent behavior expected from an uncontaminated BI. Therefore, if the controller electronics 16 determines that the first fluorescence reading from BI 26 exceeds the threshold, then controller electronics 16 provides an output on operator interface 18 indicating that the particular BI 26 for which the reading was taken has been contaminated and the efficacy of that particular sterilization cycle cannot be determined. This is indicated by blocks 62 and 64 shown in FIG. 2A.

If BI 26 has not been contaminated, controller electronics 16 preferably takes a number of readings to look for the minima in the kinetic series associated with that particular BI. In doing that, controller electronics 16 first preferably takes a number of readings looking for the negative slope typically found with this model of BI in the first three–five minutes. Then, controller electronics 16 takes a number of readings looking for a zero slope curve corresponding to the next several minutes in the kinetic series. When the zero slope is read, controller electronics 16 determines this as the local minima for that particular BI and takes a baseline fluorescence reading. This is indicated by blocks 61, 63 and 65 shown in FIG. 2A.

The baseline fluorescence reading is taken and stored by controller electronics 16 in an associated memory. The initial or baseline fluorescence reading is indicative of the autofluorescent behavior of the particular BI 26 for which the reading is being taken. In addition, unless BI 26 was contaminated prior to the sterilization cycle, the baseline or threshold reading will not include fluorescence attributable to any significant spore growth.

After the baseline reading is obtained, controller electronics 16 waits for a designated time out. The length of the time out will correspond to the particular BI type being used, and how fast spore growth activity is expected to occur. This is indicated by block 66. Such a time out may be, for example, one–three minutes, or more, as desired.

After the desired time out, another fluorescence reading is taken from BI 26. After the secondary fluorescence reading is taken from BI 26, controller electronics 16 compares that fluorescence reading with the baseline fluorescence taken for that particular BI 26 (which has been stored in memory). If controller electronics 16 determines that the secondary fluorescence reading exceeds the baseline fluorescence reading by a statistically significant amount; that means that a statistically significant amount of biological activity (spore growth) has occurred in BI 26 during the incubation cycle. Thus the sterilization cycle has not been efficacious. Controller electronics 16 therefore provides an output to operator interface 18 indicating that the sterilization cycle has not been efficacious. This is indicated by blocks 69, 70 and 72 in FIG. 2B.

Figure 2C:
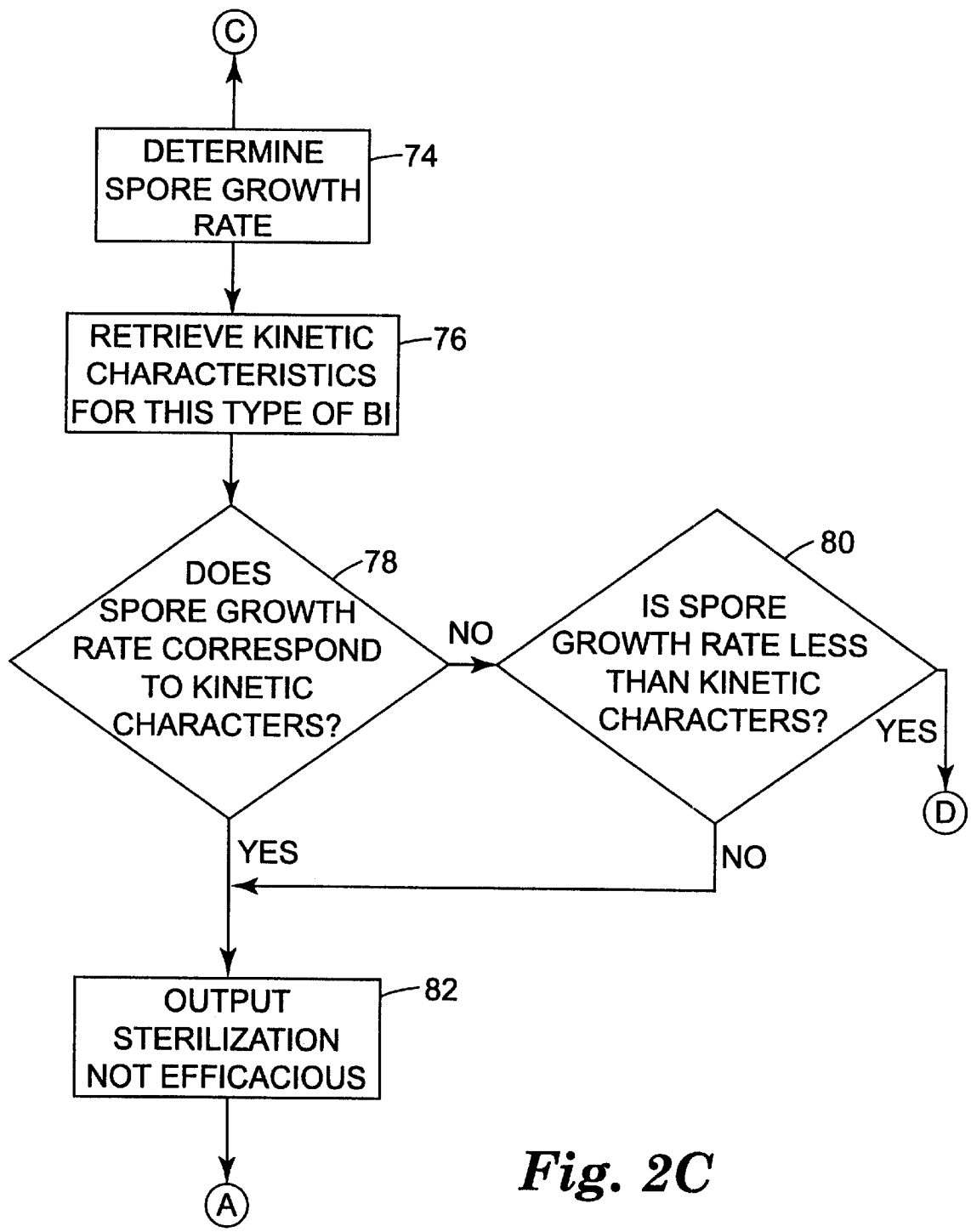

Alternatively, and as shown in FIG. 2C, controller electronics 16 can perform additional analysis on the fluorescence readings taken. For instance, FIG. 3 illustrates a family of curves for one type of biological indicator exposed to different levels of sterilant. Such curves exist or can be determined for other types of BIs as well. In the embodiment shown in FIG. 2C, controller electronics 16 determines the spore growth rate in BI 26, based on the baseline and secondary fluorescence measurements of the particular biological indicator being analyzed. This is indicated by block 74. Then, controller electronics 16 retrieves the kinetic characteristics for this type of BI. In other words, controller electronics 16 retrieves the particular family of curves (such as that shown in FIG. 3) which corresponds to this type of biological indicator. This is indicated by block 76.

Controller electronics 16 then determines whether the spore growth rate in the particular BI 26 being analyzed corresponds to the kinetic characteristics of one of the curves. If so, controller electronics 16 provides an output to operator interface 18 indicating that the sterilization cycle has, or has not, been efficacious, depending on the particular curve to which the readings correspond. If the spore growth rate does not correspond to the kinetic characteristics of the curve which is illustrative of no viable organisms, controller electronics 16 determines whether the spore growth rate for the particular BI 26 being analyzed is less than that identified by the kinetic characteristics retrieved. If not, that indicates that the spore growth rate exceeds that identified by the relevant curve corresponding to no viable organisms, and thus indicates again that the sterilization cycle has not been efficacious. Controller electronics 16 then outputs the appropriate message.

If the spore growth rate determined for the particular BI 26 under analysis is less than the kinetic characteristics identified by the curve, controller electronics 16 determines whether additional incubation is required, and, if so, the incubation cycle is continued. These steps are indicated by blocks 78, 80, and 82 shown in FIG. 2C.

It should be also be noted that controller electronics 16 may not only check the fluorescence readings to determine whether the secondary readings are in excess of the baseline fluorescence reading, but it may determine whether spore growth activity is occurring in a different way. For instance, controller electronics 16 may determine whether the curve obtained by plotting the fluorescence readings against time is positive for two, three or more consecutive reading intervals. If so, controller electronics 16 determines that this indicates positive biological activity and provides an output to operator interface 18 indicating that the sterilization cycle has not been efficacious.

Other suitable methods can also be used, such as basing the efficiatiousness determination not only on the sign of the slope, but on the magnitude of the slope as well. For instance, if the slope is very positive, this tends to more quickly indicate the presence of viable organisms than if the slope is only slightly positive.

Referring again to FIG. 2A, if the secondary fluorescence reading does not exceed the baseline fluorescence reading by a statistically significant amount, then controller electronics 16 determines whether additional incubation time is required. Depending on the particular biological indicator being analyzed, the operator may wish to incubate the biological indicator for anywhere between 5 and 15 minutes, or more. However, as indicated by the family of curves in FIG. 3, it has been observed that using this system of reading BI 26, the efficacy of the sterilization cycle can be determined for some biological indicators after only five minutes, for the vast majority of biological indicators in less than ten minutes and for substantially all biological indicators in less than fifteen minutes. The operator simply needs to incubate the biological indicator for sufficient time that an adequate confidence level is achieved which indicates that there is no spore growth activity, and that there will be none, in the particular BI 26 under analysis. This is indicated by block 84 shown in FIG. 2B. This time is preferably determined by empirical characterization studies of the various BIs to be analyzed.

Once controller electronics 16 determines that the secondary fluorescence reading has not exceeded the baseline fluorescence reading by a statistically significant amount, and once controller electronics 16 determines that no additional incubation time is required, controller electronics 16 provides an output to operator interface 18 indicating that the sterilization cycle has been efficacious. This is indicated by block 86 in FIG. 2B.

It should be noted that, while the present description has proceeded with respect to a single baseline fluorescence reading and a single secondary fluorescence reading, other methods of taking fluorescence readings can be used. For example, for each baseline or secondary fluorescence reading value, a plurality or cluster of readings can be taken within a relatively short time period. Those plurality of readings are then processed, such as averaged, in order to arrive at a single fluorescence reading value which is stored as that particular baseline or secondary fluorescence reading. For instance, in one preferred embodiment, five readings are taken within a several second time span. Those readings are then averaged to arrive at an ultimate fluorescence reading. That fluorescence reading is stored as the baseline fluorescence reading. Then, five minutes later, five more readings are taken within a several second time span and those readings are averaged. The average value is stored as the secondary fluorescence reading value. Every two minutes thereafter, five additional readings are taken and averaged to arrive at additional secondary fluorescence readings. This is repeated until the maximum incubation time period is reached.

Of course, rather than averaging the plurality of fluorescence readings, other processing techniques can also be used to arrive at an ultimate reading. For instance, high or low aberrational readings can be discarded prior to averaging, the median value can be used, or any other suitable processing can be performed.

Figure 2D:
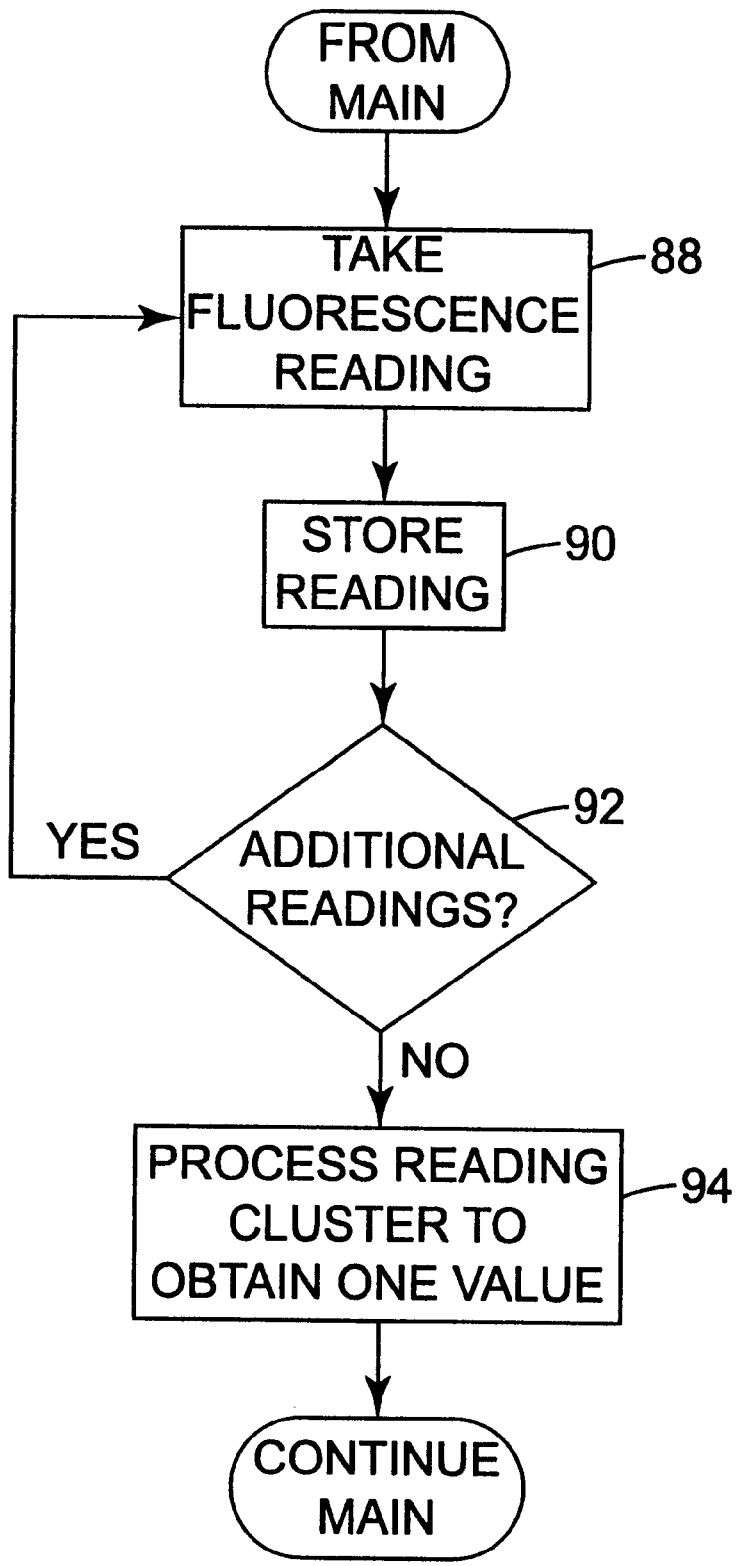

Such a system is illustrated by FIG. 2D. A first fluorescence reading is taken and stored. This is indicated by blocks 88 and 90. Controller electronics 16 then determines whether any additional fluorescence readings are to be taken at that time. If so, additional fluorescence readings are taken and stored to form a reading cluster of the desired number of closely spaced readings. This is indicated by block 92.

If no additional readings are to be taken for that particular reading cluster, the reading cluster is processed by controller electronics 16. As discussed above, this can be by averaging, taking the median value, discarding aberrational values, or other suitable processing techniques. This is indicated by block 94. The ultimate value which is the result of the processing is stored and operation of system 10 continues as set out in FIGS. 2A–2C.

Figure 4:
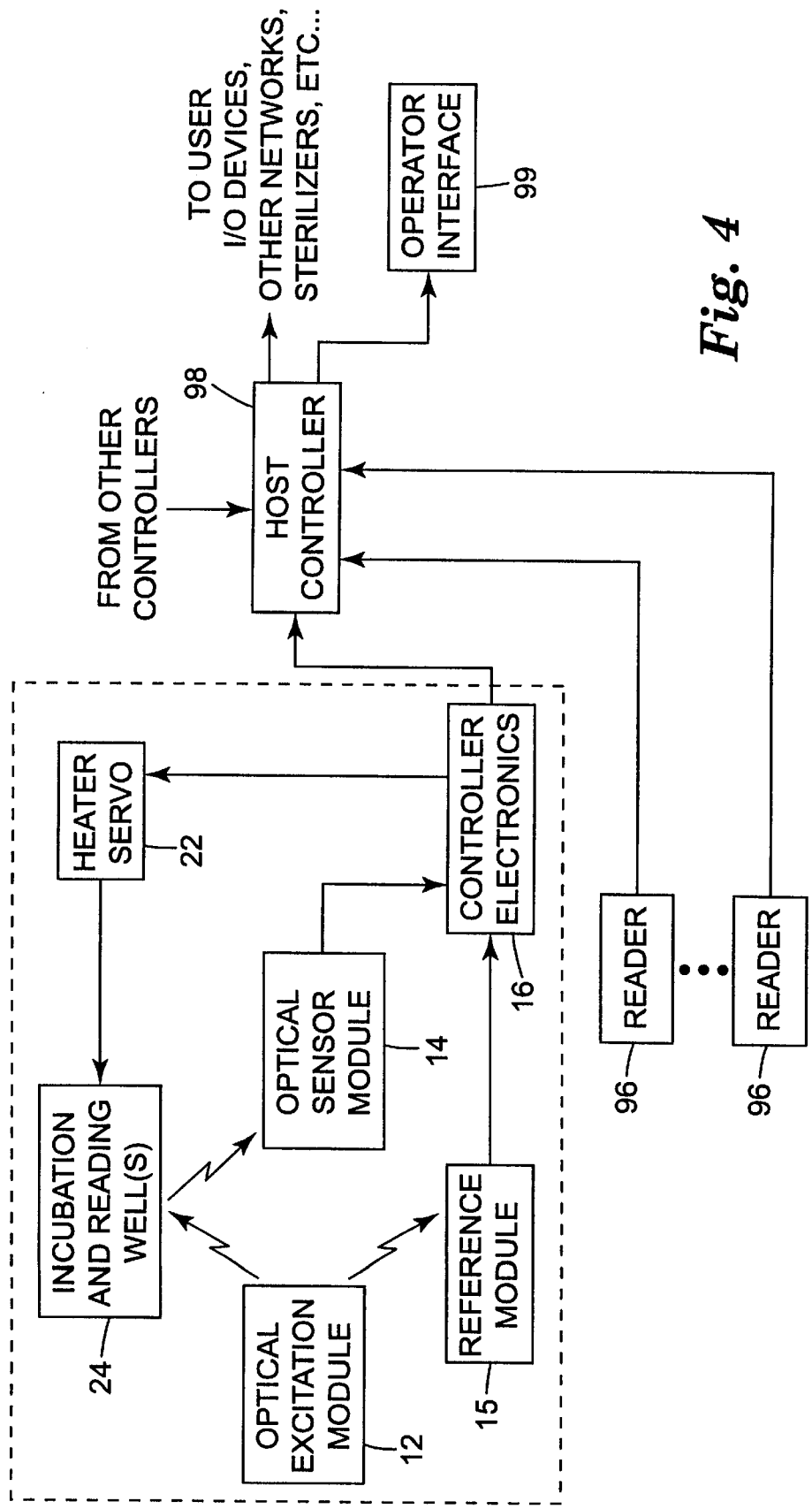
FIG. 4 is a block diagram of a plurality of biological indicator systems preferably coupled to one another in accordance with one embodiment of the present invention.

FIG. 4 illustrates a block diagram of another aspect of the present invention. In FIG. 4, a plurality of readers 96 are coupled to a host controller 98. For the purposes of description of FIG. 4, readers 96 each include electro-optical excitation module 12, electro-optical sensor module 14, reference module 15, controller electronics 16, incubator 24, and heating servo 22. Of course, each reader 96 can also include an operator interface 99. The controller electronics 16 from each reader 96 is, in turn, coupled to host controller 98 which also optionally receives inputs from other host controllers and optionally provides outputs to user I/O devices (such as operator interface 99, bar code readers and label makers) other medical institution networks, sterilizers, and any other suitable devices or networks.

The present system can also be used to incubate and read a plurality of different types of BIs. Where the various BIs require different incubation temperature, different heater servos 22 are provided along with a plurality of incubators 24. Controller electronics 16 then incubate the BIs at the appropriate temperature with suitable time out periods and reads and stores the fluorescence readings for each BI independently. Suitable outputs are provided to the operator at operator interface 18.

Thus, it can be seen that the present invention provides a system for reading conventional and commercially available biological sterilization indicators to determine the efficacy of a sterilization cycle within 15 minutes, or less. This is accomplished by simply detecting a change in the fluorescence of the biological indicator, rather than waiting for the fluorescence to reach a value which is in excess of a worst case autofluorescence exhibited by typical biological indicators. In fact, it has been observed that, using the present invention, a vast majority of biological indicators can be read in less than ten minutes.

Although the present invention has been described with reference to preferred embodiments, workers skilled in the art will recognize that changes may be made in form and detail without departing from the spirit and scope of the invention.

What is claimed is:

1. A method of determining efficacy of a sterilization cycle, the method comprising:
    selecting a test biological sterilization indicator which exhibits fluorescence in response to biological activity indicative of bacterial growth in the test biological sterilization indicator from a lot of biological sterilization indicators;
    exposing the test biological sterilization indicator to the sterilization cycle;
    placing the test biological sterilization indicator in a fluorescence reading apparatus;
    reading fluorescence from the test biological sterilization indicator to obtain a baseline fluorescence reading;
    re-reading fluorescence from the test biological sterilization indicator to obtain a second fluorescence reading;
    determining the efficacy of the sterilization cycle based on the baseline and second fluorescence readings without requiring a positive control biological sterilization indicator from the lot of biological indicators from which the test biological sterilization indicator was selected; and
    the step of reading fluorescence to obtain the baseline comprises:
        taking a plurality of preliminary fluorescence readings;
        determining whether fluorescence readings have substantially reached a minima based on the preliminary fluorescence readings; and
        performing the step of reading fluorescence from the test biological sterilization indicator to obtain a baseline fluorescence reading when the fluorescence readings have substantially reached the minima.

2. The method of claim 1 wherein reading fluorescence to obtain the baseline fluorescence reading is performed after the sterilization cycle and before any significant bacterial growth has occurred in the test biological sterilization indicator since completion of the sterilization cycle.

3. The method of claim 2 and further comprising:
    incubating the test biological sterilization indicator between obtaining the baseline fluorescence reading and obtaining the second fluorescence reading.

4. The method of claim 1 and further comprising:
    determining whether the test biological sterilization indicator is contaminated based on at least one of the plurality of preliminary fluorescence readings.

5. The method of claim 4 wherein determining whether the test biological sterilization indicator is contaminated comprises:
    determining whether the at least one of the preliminary fluorescence readings meets a first threshold level;
    and providing an indication that the test biological sterilization indicator is contaminated when the at least one of the preliminary fluorescence readings meets the first threshold level.

6. The method of claim 1 wherein determining the efficacy of the sterilization cycle comprises:
    determining whether the second fluorescence reading exceeds the baseline fluorescence reading; and
    if so, determining that the sterilization cycle was not efficacious.

7. The method of claim 6 wherein determining whether the second fluorescence reading exceeds the baseline fluorescence reading comprises the step of:
    determining whether the second fluorescence reading exceeds the baseline fluorescence reading by a statistically significant amount.

8. The method of claim 6 and further comprising:
    taking a plurality of fluorescence readings after the baseline fluorescence reading and determining whether any of the plurality of fluorescence readings exceed the baseline fluorescence reading.

9. The method of claim 1 wherein reading fluorescence and re-reading fluorescence each comprise:
    taking a plurality of fluorescence readings closely spaced in time relative to a time separating the reading and rereading steps; and
    processing the plurality of fluorescence readings to obtain an ultimate fluorescence reading.

10. A method of determining efficacy of a sterilization cycle, the method comprising:
    selecting a test biological sterilization indicator which exhibits fluorescence in response to biological activity indicative of bacterial growth in the test biological sterilization indicator from a lot of biological sterilization indicators;
    exposing the test biological sterilization indicator to the sterilization cycle;
    placing the test biological sterilization indicator in a fluorescence reading apparatus;
    reading fluorescence from the test biological sterilization indicator to obtain a baseline fluorescence reading;
    re-reading fluorescence from the test biological sterilization indicator to obtain a second fluorescence reading;
    determining the efficacy of the sterilization cycle based on the baseline and second fluorescence readings without requiring a positive control biological sterilization indicator from the lot of biological indicators from which the test biological sterilization indicator was selected;
    wherein determining the efficacy of the sterilization cycle comprises:
        extrapolating a line between the baseline and second fluorescence readings;

calculating the sign of the slope of the line; and determining the efficacy of the sterilization cycle based on the sign of the slope of the line.

11. The method of claim 10 wherein determining the efficacy of the sterilization cycle comprises:

determining that the sterilization cycle is not efficacious if the slope is positive.

12. The method of claim 10 and further comprising:

determining the magnitude of the slope; and determining the efficacy of the sterilization cycle based on the sign and the magnitude of the slope.

13. The method of claim 10 and further comprising:

determining the magnitude of the slope of the line; and determining the efficacy of the sterilization cycle based on the sign of the slope of the line and the magnitude of the slope of the line.

14. The method of claim 13 wherein determining the efficacy of the sterilization cycle based on the slope of the line comprises the steps of:

re-reading fluorescence from the biological sterilization indicator to obtain a third fluorescence reading;

extrapolating a second line between the second and third fluorescence readings;

calculating the sign of the slope of the second line extrapolated; and determining the efficacy of the sterilization cycle based on the sign of the slope of the second line and the sign of the slope of the line extrapolated between the baseline fluorescence reading and the second fluorescence reading.

15. The method of claim 14 wherein determining the efficacy of the sterilization cycle comprises the step of:

determining that the sterilization cycle was not efficacious if the sign of the slope of the second line and the sign of the slope of the line extrapolated between the baseline fluorescence reading and the second fluorescence reading is positive.

16. A method of determining efficacy of a sterilization cycle, the method comprising:

selecting a test biological sterilization indicator which exhibits a perceptible physical characteristic in response to bacterial growth therein from a lot of biological sterilization indicators;

exposing the test biological sterilization indicator to the sterilization cycle; and incubating the test biological sterilization indicator for an incubation time not in excess of approximately fifteen minutes;

then determining the efficacy of the sterilization cycle based on whether the physical characteristic is present, within approximately fifteen minutes of an end of the sterilization cycle by (a) reading the test biological sterilization indicator prior to a significant amount of bacterial growth since exposure to the sterilization cycle, (b) comparing the physical characteristic detected from the reading prior to a significant amount of bacterial growth to the physical characteristic detected after incubating for a time period; to thereby determine the efficacy of the sterilization cycle based on the comparison without requiring a positive control biological sterilization indicator from the lot of biological indicators from which the test biological sterilization indicator was selected;

wherein the step of reading the test biological sterilization indicator prior to a significant amount of bacterial growth comprises the steps of determining whether the physical characteristic has reached a local minima; and taking a baseline physical characteristic reading at substantially the time that the physical characteristic has reached the local minima.

17. The method of claim 16 wherein determining the efficacy of the sterilization cycle comprises:

determining the efficacy of the sterilization cycle, based on whether the physical characteristic is present, within approximately ten minutes of an end of the sterilization cycle.

18. The method of claim 16 wherein the physical characteristic is fluorescence, the step of determining the efficacy of the sterilization cycle comprises:

taking a secondary fluorescence reading after the baseline fluorescence reading; and determining the efficacy of the sterilization cycle, based on whether the secondary fluorescence reading exceeds the baseline fluorescence reading, within approximately five minutes of the fluorescence readings reaching the local minima.

19. A method of determining efficacy of a sterilization cycle, the method comprising:

selecting a test biological sterilization indicator which exhibits fluorescence in response to biological activity indicative of bacterial growth in the test biological sterilization indicator from a lot of biological sterilization indicators;

exposing the test biological sterilization indicator to the sterilization cycle;

placing the test biological sterilization indicator in a fluorescence reading apparatus;

reading autofluorescence from the test biological sterilization indicator to obtain an autofluorescence reading;

re-reading fluorescence from the test biological sterilization indicator within fifteen minutes of reading autofluorescence to obtain a second fluorescence reading;

determining the efficacy of the sterilization cycle based on the autofluorescence reading and the second fluorescence reading without requiring a positive control biological sterilization indicator from the lot of biological indicators from which the test biological sterilization indicator was selected; and wherein the step of determining the efficacy of the sterilization cycle includes the step of calculating the sign of the slope of the line between the autofluorescence and second fluorescence readings and determining the efficacy of the sterilization cycle based on the sign of the slope of the line.

20. The method of claim 19 wherein reading the autofluorescence is performed after the sterilization cycle and before any significant bacterial growth has occurred in the test biological sterilization indicator since completion of the sterilization cycle.

21. The method of claim 20 and further comprising:

incubating the test biological sterilization indicator between reading the autofluorescence and obtaining the second fluorescence reading.

22. A method of determining efficacy of a sterilization cycle, the method comprising the steps of:

providing a plurality of reference sterilization indicators;

subjecting said reference sterilization indicators to a variety of sterilization cycles including non-lethal sterilization cycles and lethal sterilization cycles to obtain reference information;

providing a test sterilization indicator which exhibits a physical characteristic indicative of bacterial growth in a biological sterilization indicator;

exposing the test sterilization indicator to a sterilization cycle;

placing the test sterilization indicator in a physical characteristic reading apparatus;

obtaining test sterilization indicator information by:
(a) reading the physical characteristic of the test sterilization indicator to obtain a first physical characteristic reading; and
(b) re-reading physical characteristic from the test sterilization indicator to obtain a second physical characteristic reading; and determining the efficacy of the sterilization cycle by (i) comparing the test sterilization indicator information to the reference information, and (ii) determining whether the test sterilization indicator information corresponds to reference information relating to a lethal sterilization cycle or a non-lethal sterilization cycle and indicating the efficacy of the sterilization cycle based on that determination.

* * * * *